(12) United States Patent
Kappus et al.

(10) Patent No.: US 10,080,606 B2
(45) Date of Patent: Sep. 25, 2018

(54) METHOD OF FORMING A MEMBER OF AN END EFFECTOR

(71) Applicant: COVIDIEN LP, Mansfield, MA (US)

(72) Inventors: John J. Kappus, Denver, CO (US); David N. Heard, Boulder, CO (US); William Scott Darrow, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 454 days.

(21) Appl. No.: 14/802,222

(22) Filed: Jul. 17, 2015

(65) Prior Publication Data

US 2016/0074099 A1    Mar. 17, 2016

Related U.S. Application Data

(60) Provisional application No. 62/051,504, filed on Sep. 17, 2014.

(51) Int. Cl.
| | |
|---|---|
| *A61B 18/14* | (2006.01) |
| *A61B 18/00* | (2006.01) |
| *A61B 17/00* | (2006.01) |
| *A61B 34/35* | (2016.01) |

(52) U.S. Cl.
CPC .......... *A61B 18/1445* (2013.01); *A61B 34/35* (2016.02); *A61B 2017/0088* (2013.01); *A61B 2017/00526* (2013.01); *A61B 2018/00083* (2013.01); *A61B 2018/00303* (2013.01); *A61B 2018/00607* (2013.01); *A61B 2018/00791* (2013.01);
(Continued)

(58) Field of Classification Search
CPC ... B29C 45/14; B29C 43/18; B29C 2043/181; A61B 18/085; A61B 18/087; A61B 2018/087; A61B 18/1442; A61B 18/1445; A61B 18/14; A61B 18/1402; A61B 18/12; A61B 17/00; A61B 2017/00526; A61B 2018/1452; A61B 2018/126; A61B 2018/00607
See application file for complete search history.

(56) References Cited

U.S. PATENT DOCUMENTS

| | | | |
|---|---|---|---|
| D249,549 | S | 9/1978 | Pike |
| D263,020 | S | 2/1982 | Rau, III |
| D295,893 | S | 5/1988 | Sharkany et al. |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

Peterson et al. "Comparison of Healing Process Following Ligation with Sutures and Bipolar Vessel Sealing" Surgical Technology International (2001).

(Continued)

*Primary Examiner* — Sarang Afzali

(57) ABSTRACT

A method of forming a jaw member of an end effector includes providing a metal support base; engaging a plurality of ceramic stops to the metal support base; and coupling an insulative plate and a sealing plate to the metal support base by aligning the plurality of ceramic stops through a plurality of openings defined in the insulative plate and a plurality of openings defined in the sealing plate.

10 Claims, 4 Drawing Sheets

(52) U.S. Cl.
CPC ............... *A61B 2018/00875* (2013.01); *A61B 2018/1455* (2013.01)

(56) References Cited

U.S. PATENT DOCUMENTS

| | | | |
|---|---|---|---|
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,700,261 A | 12/1997 | Brinkerhoff |
| H1745 H | 4/1998 | Paraschac |
| D402,028 S | 12/1998 | Grimm et al. |
| D408,018 S | 4/1999 | McNaughton |
| 5,891,142 A | 4/1999 | Eggers et al. |
| D416,089 S | 11/1999 | Barton et al. |
| 6,030,384 A | 2/2000 | Nezhat |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,648,883 B2 | 11/2003 | Francischelli et al. |
| 6,663,627 B2 | 12/2003 | Francischelli et al. |
| 6,723,092 B2 | 4/2004 | Brown et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,926,716 B2 | 8/2005 | Baker et al. |
| D509,297 S | 9/2005 | Wells |
| 7,029,470 B2 | 4/2006 | Francischelli et al. |
| D525,361 S | 7/2006 | Hushka |
| 7,083,619 B2 | 8/2006 | Truckai et al. |
| 7,090,673 B2 | 8/2006 | Dycus et al. |
| 7,094,235 B2 | 8/2006 | Francischelli |
| 7,101,371 B2 | 9/2006 | Dycus et al. |
| D531,311 S | 10/2006 | Guerra et al. |
| 7,131,971 B2 | 11/2006 | Dycus et al. |
| D533,274 S | 12/2006 | Visconti et al. |
| D533,942 S | 12/2006 | Kerr et al. |
| D535,027 S | 1/2007 | James et al. |
| 7,169,146 B2 | 1/2007 | Truckai et al. |
| D538,932 S | 3/2007 | Malik |
| 7,186,253 B2 | 3/2007 | Truckai et al. |
| 7,189,233 B2 | 3/2007 | Truckai et al. |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,250,048 B2 | 7/2007 | Francischelli et al. |
| 7,255,697 B2 | 8/2007 | Dycus et al. |
| D564,662 S | 3/2008 | Moses et al. |
| D567,943 S | 4/2008 | Moses et al. |
| 7,354,440 B2 | 4/2008 | Truckal et al. |
| 7,367,972 B2 | 5/2008 | Francischelli et al. |
| 7,381,209 B2 | 6/2008 | Truckai et al. |
| D575,395 S | 8/2008 | Hushka |
| D575,401 S | 8/2008 | Hixson et al. |
| D582,038 S | 12/2008 | Swoyer et al. |
| 7,473,253 B2 * | 1/2009 | Dycus ................. A61B 18/1445 606/51 |
| 7,632,269 B2 | 12/2009 | Truckai et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,731,717 B2 | 6/2010 | Odom et al. |
| 7,744,562 B2 | 6/2010 | Jahns et al. |
| D621,503 S | 8/2010 | Otten et al. |
| 7,776,036 B2 | 8/2010 | Schechter et al. |
| 7,794,461 B2 | 9/2010 | Eder et al. |
| 7,799,026 B2 | 9/2010 | Schechter et al. |
| 7,803,156 B2 | 9/2010 | Eder et al. |
| D627,462 S | 11/2010 | Kingsley |
| D628,289 S | 11/2010 | Romero |
| D628,290 S | 11/2010 | Romero |
| 7,824,399 B2 | 11/2010 | Francischelli et al. |
| D630,324 S | 1/2011 | Reschke |
| 7,955,331 B2 | 6/2011 | Truckai et al. |
| D649,249 S | 11/2011 | Guerra |
| D649,643 S | 11/2011 | Allen, IV et al. |
| D661,394 S | 6/2012 | Romero et al. |
| 8,535,312 B2 | 9/2013 | Horner |
| 8,679,140 B2 | 3/2014 | Butcher |
| RE44,834 E | 4/2014 | Dumbauld et al. |
| 8,747,434 B2 | 6/2014 | Larson et al. |
| 8,752,264 B2 | 6/2014 | Ackley et al. |
| 8,887,373 B2 | 11/2014 | Brandt et al. |
| 8,920,461 B2 | 12/2014 | Unger et al. |
| 8,939,975 B2 | 1/2015 | Twomey et al. |
| 8,961,513 B2 | 2/2015 | Allen, IV et al. |
| 8,961,514 B2 | 2/2015 | Garrison |
| 8,968,298 B2 | 3/2015 | Twomey |
| 8,968,311 B2 | 3/2015 | Allen, IV et al. |
| 8,968,313 B2 | 3/2015 | Larson |
| 8,968,360 B2 | 3/2015 | Garrison et al. |
| 9,458,876 B2 * | 10/2016 | Morris ................. F16B 39/284 |
| 2007/0106297 A1 | 5/2007 | Dumbauld et al. |
| 2007/0270795 A1 | 11/2007 | Francischelli et al. |
| 2008/0147062 A1 | 6/2008 | Truckai et al. |
| 2009/0082767 A1 | 3/2009 | Unger et al. |
| 2010/0076432 A1 | 3/2010 | Horner |
| 2010/0179540 A1 | 7/2010 | Marczyk et al. |
| 2010/0179545 A1 | 7/2010 | Twomey et al. |
| 2011/0004208 A1 | 1/2011 | Truckai et al. |
| 2011/0270245 A1 | 11/2011 | Horner et al. |
| 2011/0270251 A1 | 11/2011 | Horner et al. |
| 2013/0185922 A1 * | 7/2013 | Twomey ............ A61B 18/1445 29/527.1 |
| 2013/0190753 A1 * | 7/2013 | Garrison ................ A61B 17/29 606/41 |
| 2013/0190755 A1 * | 7/2013 | Deborski ............... A61B 18/14 606/41 |
| 2013/0190760 A1 * | 7/2013 | Allen, IV ........... A61B 18/1442 606/52 |
| 2013/0197503 A1 * | 8/2013 | Orszulak ............ A61B 18/1206 606/33 |
| 2013/0218198 A1 * | 8/2013 | Larson ............... A61B 18/1445 606/206 |
| 2013/0218199 A1 * | 8/2013 | Kerr ....................... A61B 17/29 606/206 |
| 2013/0219691 A1 * | 8/2013 | Reschke ............. A61B 18/1442 29/527.4 |
| 2013/0226177 A1 * | 8/2013 | Brandt ............... A61B 18/1442 606/49 |
| 2013/0226178 A1 * | 8/2013 | Brandt ............... A61B 18/1442 606/49 |
| 2013/0226226 A1 * | 8/2013 | Garrison ............ A61B 18/1445 606/206 |
| 2013/0232753 A1 * | 9/2013 | Ackley .............. A61B 18/1442 29/407.05 |
| 2013/0238016 A1 * | 9/2013 | Garrison ................ A61B 17/29 606/205 |
| 2013/0245623 A1 * | 9/2013 | Twomey ............. A61B 18/148 606/46 |
| 2013/0253489 A1 * | 9/2013 | Nau, Jr. ................ A61B 18/22 606/16 |
| 2013/0255063 A1 * | 10/2013 | Hart ................... A61B 18/1445 29/505 |

(56) References Cited

U.S. PATENT DOCUMENTS

| | | | | |
|---|---|---|---|---|
| 2013/0274736 A1* | 10/2013 | Garrison | ............ | A61B 18/1445 606/41 |
| 2013/0289561 A1* | 10/2013 | Waaler | ............... | A61B 18/1477 606/42 |
| 2013/0296848 A1* | 11/2013 | Allen, IV | ........... | A61B 18/1445 606/41 |
| 2013/0296856 A1* | 11/2013 | Unger | ................. | A61B 17/2816 606/52 |
| 2013/0296922 A1* | 11/2013 | Allen, IV | ........... | A61B 18/1445 606/205 |
| 2013/0296923 A1* | 11/2013 | Twomey | ............ | A61B 18/1442 606/205 |
| 2013/0304058 A1* | 11/2013 | Kendrick | ................ | A61B 17/29 606/41 |
| 2013/0304059 A1* | 11/2013 | Allen, IV | ............. | A61B 17/285 606/41 |
| 2013/0304066 A1* | 11/2013 | Kerr | ................... | A61B 18/1445 606/42 |
| 2013/0325043 A1* | 12/2013 | Butcher | ............... | A61B 17/122 606/157 |
| 2013/0325057 A1* | 12/2013 | Larson | ............... | A61B 18/1445 606/205 |
| 2013/0331837 A1* | 12/2013 | Larson | ............... | A61B 18/1447 606/45 |
| 2013/0345706 A1* | 12/2013 | Garrison | ............ | A61B 18/1447 606/51 |
| 2014/0005663 A1* | 1/2014 | Heard | ................ | A61B 18/1445 606/41 |
| 2014/0005666 A1* | 1/2014 | Moua | ................... | A61B 17/295 606/45 |
| 2014/0025059 A1* | 1/2014 | Kerr | ....................... | A61B 18/14 606/33 |
| 2014/0025060 A1* | 1/2014 | Kerr | ....................... | A61B 18/14 606/33 |
| 2014/0025066 A1* | 1/2014 | Kerr | .................... | A61B 18/1477 606/34 |
| 2014/0025067 A1* | 1/2014 | Kerr | .................... | A61B 18/1445 606/41 |
| 2014/0025073 A1* | 1/2014 | Twomey | ............. | A61B 18/1442 606/51 |
| 2014/0031821 A1* | 1/2014 | Garrison | .............. | A61B 18/085 606/52 |
| 2014/0031860 A1* | 1/2014 | Stoddard | ............ | A61B 17/32009 606/205 |
| 2015/0112337 A1 | 4/2015 | Twomey et al. | | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| EP | 1486177 | 6/2004 |
| EP | 1810625 | 7/2007 |
| EP | 1810625 A1 | 7/2007 |
| EP | 2377480 A1 | 10/2011 |
| EP | 2382937 A1 | 11/2011 |
| EP | 2436330 A1 | 4/2012 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001-03400 | 4/2001 |
| JP | 2001128990 A | 5/2001 |
| JP | 2001-190564 A | 7/2001 |
| JP | 2001-3400 | 11/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 2005/110264 A2 | 11/2005 |
| WO | 2006021269 A1 | 3/2006 |
| WO | 08/040483 A1 | 4/2008 |
| WO | 2008040483 A1 | 4/2008 |

OTHER PUBLICATIONS

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectomy" American College of Surgeons (ACS) Clinicla Congress Poster (2000).

(56) References Cited

OTHER PUBLICATIONS

Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
E. David Crawford "Evaluation of a New Vessel Sealing Device in Urologic Cancer Surgery", 2000.
Burdette et al. "In Vivo Probe Measurement Technique for Determining Dielectric Properties at VHF Through Microwave Frequencies", IEEE Transactions on Microwave Theory and Techniques, vol. TT-28, No. 4, Apr. 1980 pp. 414-427.
Extended European Search Report dated Oct. 11, 2013 for EP 13 17 6829.
U.S. Appl. No. 08/956,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.

(56) References Cited

OTHER PUBLICATIONS

U.S. Appl. No. 13/741,550, filed Jan. 15, 2013, Deborski.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/853,259, filed Mar. 29, 2013, Garrison.
U.S. Appl. No. 13/853,273, filed Mar. 29, 2013, Kerr.
U.S. Appl. No. 13/853,339, filed Mar. 29, 2013, Reschke.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Extended European Search Report dated Oct. 11, 2013 for EP 13 17 6829.3; 10 pages.
Tinckler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
"Reducing Needlestick Injuries in the Operating Room", 2001.
E. David Crawford "Use of a Novel Vessel Sealing Technology in Management of the Dorsal Veinous Complex", 2000.
U.S. Appl. No. 13/711,201, filed Dec. 31, 2012, Siebrecht.

\* cited by examiner

METHOD OF FORMING A MEMBER OF AN END EFFECTOR

CROSS REFERENCE TO RELATED APPLICATION

The present application claims the benefit of and priority to U.S. Provisional Application Ser. No. 62/051,504, filed on Sep. 17, 2014, the entire contents of which are incorporated herein by reference.

BACKGROUND

The present disclosure relates to methods of forming components of surgical instruments and, more particularly, to methods of forming jaw members having ceramic rods that act as a guide during assembly of the jaw members, control a gap distance between the jaw members, and provide electrical insulation between the jaw members.

TECHNICAL FIELD

Electrosurgical instruments, e.g., electrosurgical forceps, utilize both mechanical clamping action and electrical energy to effect hemostasis by heating tissue to coagulate and/or cauterize tissue. Certain surgical procedures require more than simply cauterizing tissue and rely on the unique combination of clamping pressure, precise electrosurgical energy control, and gap distance (i.e., distance between opposing jaw members when closed about tissue) to "seal" tissue.

One method of controlling the gap distance uses one or more ceramic dots or stop members on one or both jaw members. The stop members are typically deposited atop components of one or more jaw members, e.g., vapor deposited onto sealing plates. The stop members project from the tissue engaging surface of one or both jaw members and control the separation distance between opposing jaw members when closed about tissue. Since the stop members are typically made from ceramic, the stop members are stable at elevated temperatures and usually exhibit low thermal and electrical conductivities. In addition, ceramic materials have high melting points and are resistant to oxidation, corrosion, or other forms of degradation to which metals are usually more prone. However, stop members are usually applied to the sealing plate using a process involving very high temperatures, which limit the material that may be used for the sealing plates.

SUMMARY

In one aspect of the present disclosure, a method of forming a jaw member of an end effector is provided. The method includes providing a metal support base, an insulative plate having a plurality of openings defined therethrough, and a sealing plate having a plurality of openings defined therethrough. A plurality of ceramic stops having a predetermined length are engaged to the metal support base. The insulative plate and the sealing plate are coupled to the metal support base by aligning the plurality of ceramic stops through the plurality of openings defined in the insulative plate and the plurality of openings defined in the sealing plate such that a second end of each ceramic stop projects a predetermined distance relative to a tissue-engaging surface of the sealing plate.

In some embodiments, the method may further include overmolding an insulative housing around the metal support base.

In some embodiments, the insulative plate may be formed by injection molding.

In some embodiments, each of the plurality of ceramic stops may have a cylindrical configuration. Each of the plurality of ceramic stops may define a longitudinal axis therealong and the tissue-engaging surface of each of the plurality of ceramic stops may define a plane in perpendicular relation to each respective longitudinal axis.

In some embodiments, the insulative plate may be fabricated from plastic.

In some embodiments, the method may further include forming a longitudinal knife slot through each of the insulative plate and the sealing plate and aligning the slots in registration with one another. The plurality of openings of the insulative plate and the plurality of openings of the sealing plate may be formed adjacent each respective longitudinal knife slot.

In some embodiments, upon coupling the insulative plate and the sealing plate to the metal support base the plurality of ceramic stops may project from the sealing plate about 0.001 inches to about 0.006 inches.

In another aspect of the present disclosure, another method of forming a jaw member of an end effector is provided. The method includes providing a metal support base, an insulative plate having a plurality of openings defined therethrough, and a sealing plate having a plurality of openings defined therethrough. The insulative plate and the sealing plate are coupled to the metal support base. A plurality of ceramic stops are guided through the plurality of openings defined in the insulative plate and the plurality of openings defined in the sealing plate and into engagement with the metal support base such that a second end of each ceramic stop projects a predetermined distance relative to a tissue-engaging surface of the sealing plate.

In some embodiments, the method may further include overmolding an insulative housing around the metal support base. The plurality of ceramic stops may be placed into engagement with the metal support base concurrently with overmolding the insulative housing around the metal support base.

BRIEF DESCRIPTION OF THE DRAWINGS

Embodiments of the present disclosure are described herein with reference to the accompanying drawings, wherein.

DETAILED DESCRIPTION

Figure 1:
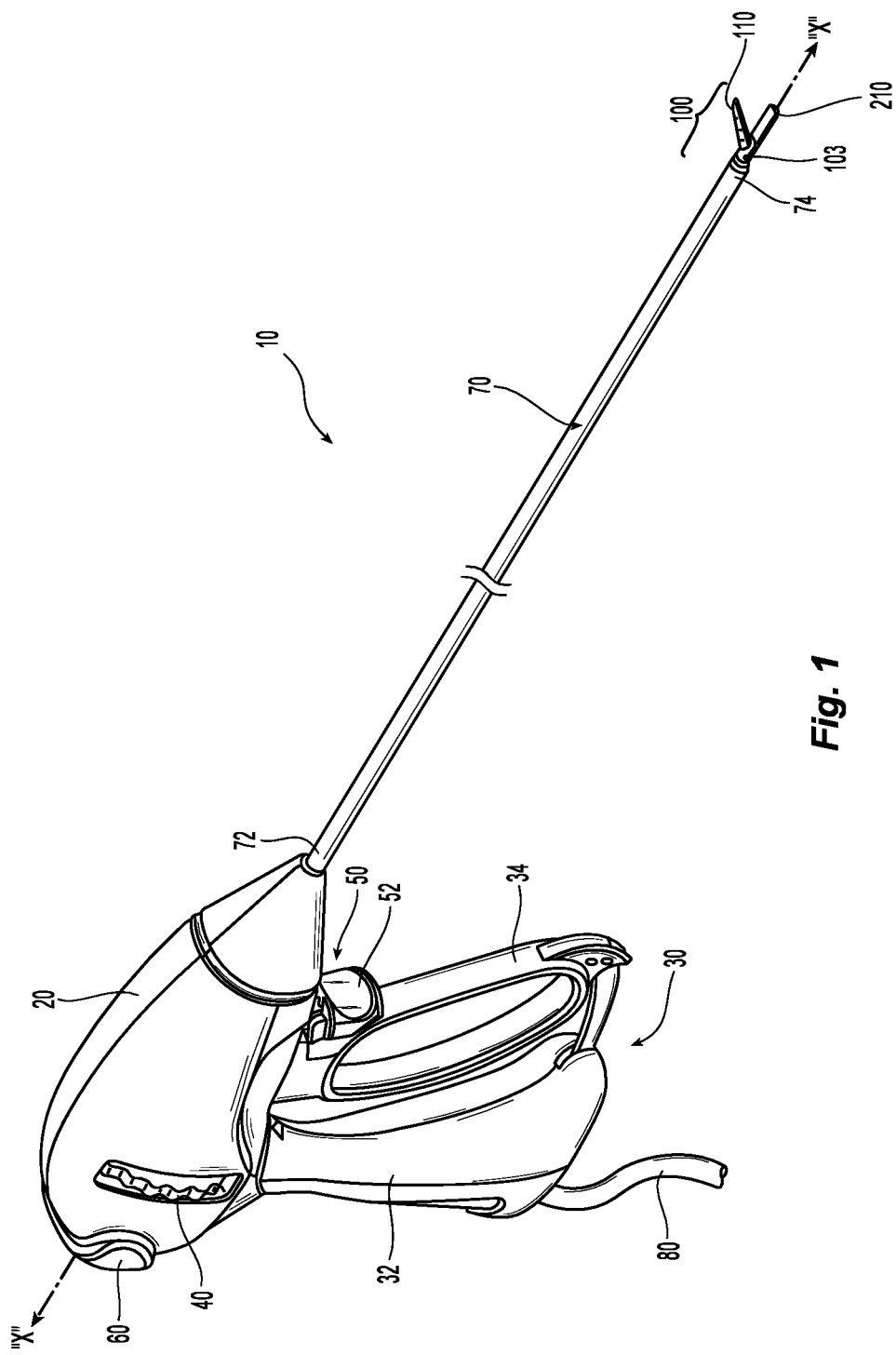
FIG. 1 is a perspective view of an endoscopic surgical instrument configured for use in accordance with the present disclosure.
Figure 2:
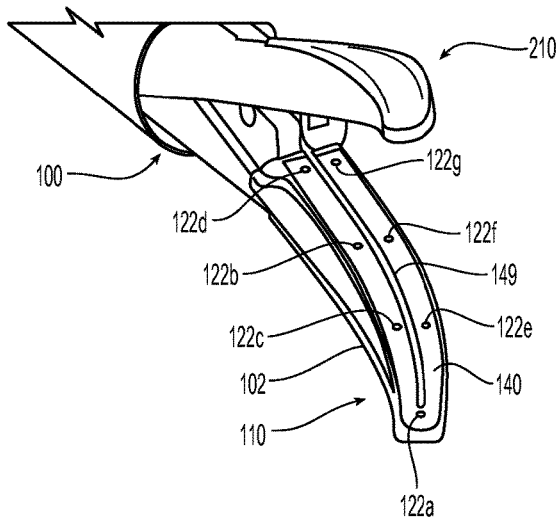
FIG. 2 is a front, perspective view of an end effector of the surgical instrument shown in FIG. 1.
Figure 3:
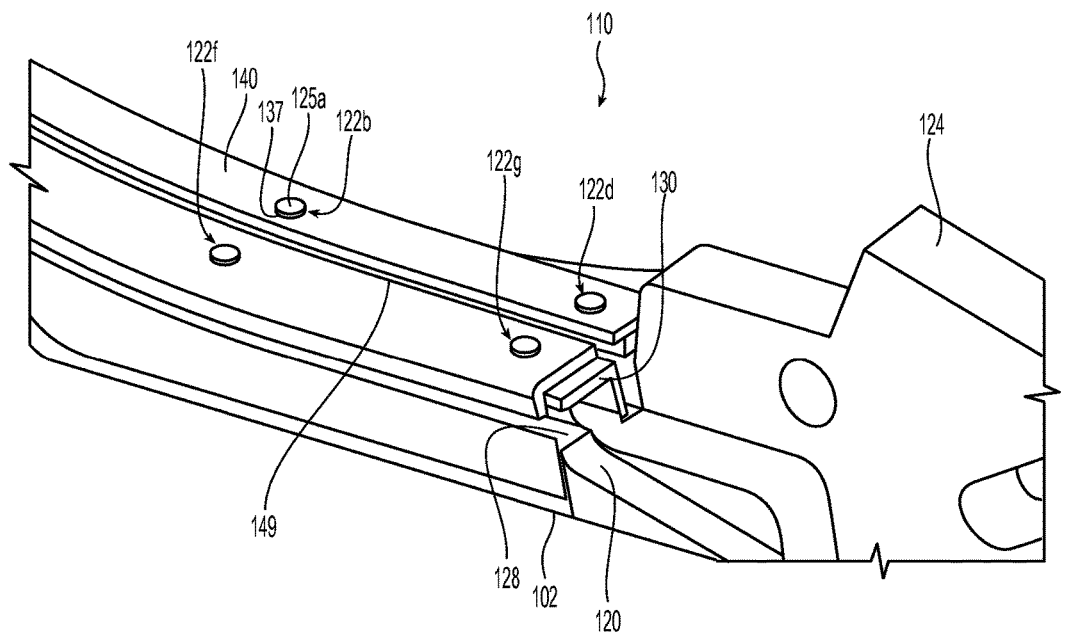
FIG. 3 is an enlarged, perspective view of a jaw member of the end effector shown in FIG. 2.

Embodiments of the presently disclosed electrosurgical instrument are described in detail with reference to the drawings, in which like reference numerals designate identical or corresponding elements in each of the several views.

As used herein, the term "distal" refers to that portion of the surgical instrument or component thereof, farther from the user, while the term "proximal" refers to that portion of the surgical instrument, or component thereof, closer to the user.

With reference to FIG. 1, a surgical instrument, such as, for example, an endoscopic forceps 10 is provided. For the purposes herein, either an endoscopic instrument or an open instrument (not explicitly shown) may be utilized in accordance with the present disclosure. Forceps 10 includes a pair of jaw members 110, 210 each having a plurality of stop members, such as, for example, ceramic stops 122a-g, 222a-g (FIGS. 4A and 4B) connected directly to metal support bases 120, 220 of respective jaw members 110, 210. Ceramic stops 122a-g, 222a-g (FIGS. 4A and 4B) being directly connected to metal support bases 120, 220 of respective jaw members 110, 210 assist in the assembly of jaw members 110, 210 and provide a separation or gap distance between jaw members 110, 210 when approximated, as described in greater detail below.

With continued reference to FIG. 1, forceps 10 defines a longitudinal axis "X-X" and includes a housing 20, a handle assembly 30, a rotating assembly 40, a trigger assembly 50, a switch 60, a shaft 70 extending distally from housing 20, and an end effector assembly 100. Shaft 70 has a proximal end 72 that mechanically engages housing 20 and a distal end 74 configured to mechanically engage end effector assembly 100. Housing 20 contains the internal working components of forceps 10. Reference may be made to commonly-owned U.S. Pat. No. 7,156,846, the entire contents of which are hereby incorporated by reference herein, for a detailed description of the internal working components of housing 20.

End effector assembly 100 includes the pair of opposing jaw members 110 and 210 coupled to distal end 74 of shaft 70. Jaw members 110, 210 are moveable between a spaced-apart position and an approximated position for grasping tissue therebetween. End effector assembly 100 is designed as a unilateral assembly, e.g., jaw member 210 is fixed relative to shaft 70 and jaw member 110 is moveable about a pivot 103 relative to shaft 70 and fixed jaw member 210. In some embodiments, end effector assembly 100 may be configured as a bilateral assembly, e.g., where both jaw member 110 and jaw member 210 are moveable about pivot 103 relative to one another and to shaft 70.

With continued reference to FIG. 1, forceps 10 also includes an electrosurgical cable 80 that connects forceps 10 to a generator (not explicitly shown) or other suitable power source. In some embodiments, forceps 10 may be configured as a battery-powered instrument. Cable 80 includes a wire or wires (not explicitly shown) extending therethrough that has sufficient length to extend through shaft 70 in order to provide electrical energy to at least one of jaw members 110 and 210 of end effector assembly 100. Trigger 52 of trigger assembly 50 may be selectively depressed to advance a knife (not explicitly shown) between jaw members 110, 210 to cut tissue grasped therebetween. Switch 60 is selectively activated to supply electrosurgical energy to jaw members 110, 210.

Handle assembly 30 includes a fixed handle 32 and a moveable handle 34. Fixed handle 32 is integrally associated with housing 20 and moveable handle 34 is moveable relative to fixed handle 32. Rotating assembly 40 is rotatable in either direction about longitudinal axis "X-X" to rotate end effector 100 about longitudinal axis "X-X." Moveable handle 34 of handle assembly 30 is coupled to a drive assembly (not explicitly shown) that, together, mechanically cooperate to impart movement of jaw members 110 and 210 between the spaced-apart position and the approximated position to grasp tissue disposed between jaw members 110, 210. Moveable handle 34 is biased from fixed handle 32 and, correspondingly, jaw members 110, 210 are in the spaced-apart position. Moveable handle 34 is compressible from a spaced-apart position to a compressed position corresponding to the approximated position of jaw members 110, 210.

With reference to FIGS. 2, 3, 4A, and 4B, jaw members 110, 210 each include an insulative housing 102, 202, metal support base 120, 220, an insulative plate 130, 230, and a sealing plate 140, 240, respectively. As jaw members 110, 210 clamp together around tissue, stop members 122a-g, 222a-g maintain a gap distance between jaw members 110, 210. In some embodiments, the gap distance may be about 0.001 inches to about 0.006 inches.

Figure 4A:
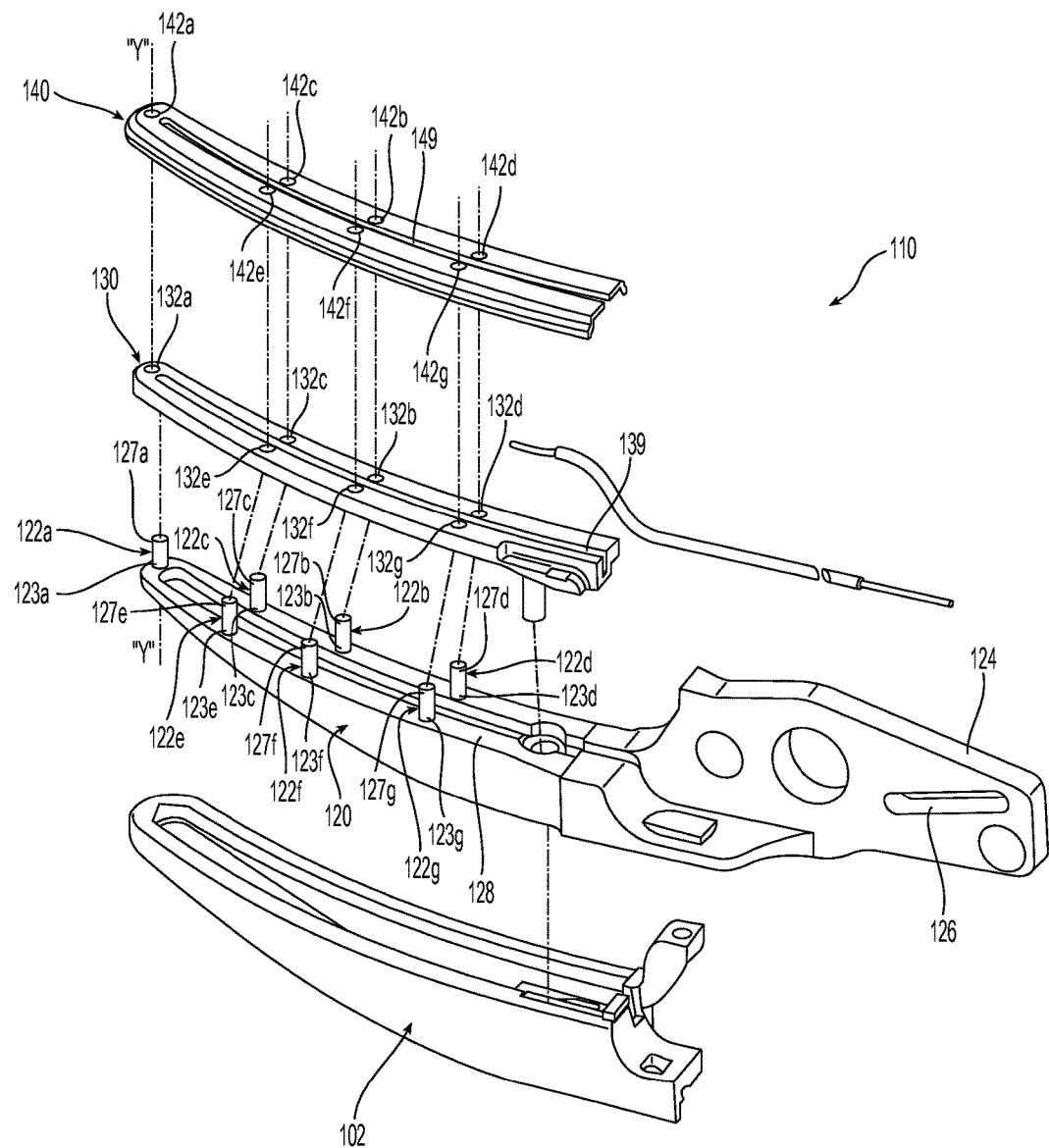
FIG. 4A is an exploded view of the jaw member shown in FIG. 3.
Figure 4B:
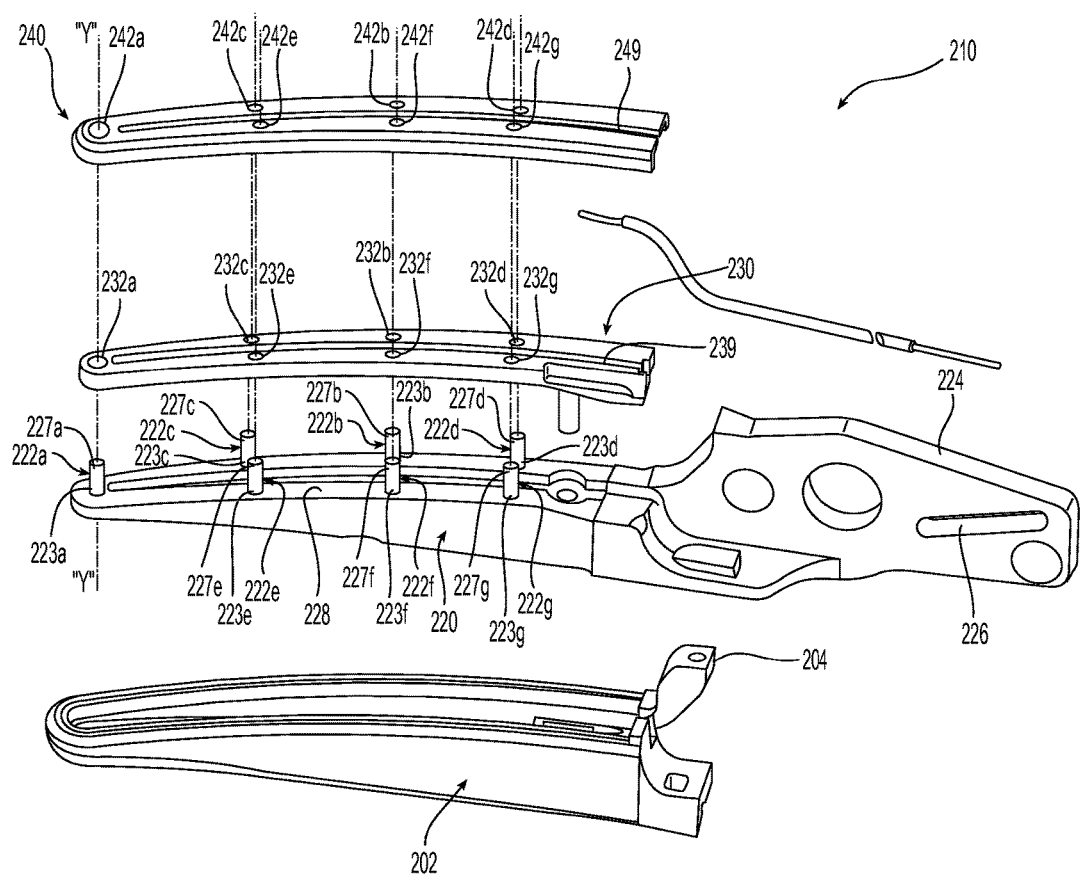
FIG. 4B is an exploded view of another jaw member of the end effector shown in FIG. 2.

With reference to FIGS. 4A and 4B, metal support bases 120, 220 include proximally extending flanges 124, 224, respectively. Flanges 124, 224 each include an elongated angled cam slot 126, 226 defined therethrough configured to engage an actuator rod (not explicitly shown) that drives the opening and closing of the jaw members 110, 210 as the actuator rod moves through cam slots 126, 226. Metal support bases 120, 220 are configured to support insulative plates 130, 230, respectively, which, in turn, support electrically conductive sealing plates 140, 240 thereon.

Metal support bases 120, 220 further include respective tissue-oriented surfaces 128, 228. Tissue-oriented surfaces 128, 228 have the plurality of ceramic stops 122a-g, 222a-g, respectively, extending perpendicularly therefrom. Ceramic stops 122a-g, 222a-g have electrically insulative properties and are configured to electrically insulate jaw members 110, 210 when no tissue is disposed therebetween, act as an isolating spacer between jaw members 110, 210 to prevent tissue from being over-compressed, assist the user in gripping tissue during grasping, and assist in the assembly of jaw members 110, 210 by acting as guide-posts along which insulative plates 130, 230 and sealing plates 140, 240 may be guided into engagement with metal support bases 120, 220, as described in greater detail below.

Ceramic stops 122a-g, 222a-g are relatively small in size to reduce the effect of ceramic stops 122a-g, 222a-g on tissue sealing performance. For example, ceramic stops 122a-g, 222a-g may range from about 0.020 inches to about 0.050 inches in diameter. However, the size of ceramic stops 122a-g, 222a-g can vary based on the size of jaw members 110, 210. In the illustrated embodiment, each ceramic stop 122a-g, 222a-g is generally cylindrical and has a first end 123a-g, 223a-g and a second end 127a-g, 227a-g. Each ceramic stop 122a-g, 222a-g defines a longitudinal axis therethrough, e.g., axis "Y-Y" of ceramic stop 122a. First ends, e.g., end 123a, 223a of each respective ceramic stop 122a, 222a are directly connected to tissue-oriented surfaces 128, 228 of jaw members 110, 210. First ends 123a, 223a of each ceramic stop 122a-g, 222a-g may be monolithically formed with, integrally connected to, or fastened to respective tissue-oriented surfaces 128, 228 of jaw members 110, 210 via various fastening engagements, such as, for example, adhesives, ultrasonic welding, snap-fit engagement, etc.

Second ends, e.g., second ends 127a, 227a of each respective ceramic stop 122a-g, 222a-g includes a planar tissue-contacting or tissue-engaging surface 125a (FIG. 3) that defines a plane substantially parallel with tissue-oriented surfaces 128, 228 of respective jaw members 110, 210. The plane of each planar tissue-contacting surface 125a (FIG. 3) is in perpendicular relation to each respective longitudinal axis "Y-Y" of each ceramic stop 122a-g, 222a- g. Each planar tissue-contacting surface, e.g., surface 125a (FIG. 3) of respective ceramic stops 122a-g, 222a-g has a pointed/squared circumferential edge 137 (FIG. 3) designed to improve grasping and holding of slippery tissue between jaw members 110, 210. Connecting ceramic stops 122a-g, 222a-g directly to metal support bases 120, 220 more closely controls the height of the ceramic stops 122a-g, 222a-g relative to the components that drive the actuation of jaw members 110, 210, namely, the jaw pivot 103 and cam slots 126, 226 of metal support bases 120, 220.

With reference to FIGS. 4A and 4B, insulative plates 130, 230 and sealing plates 140, 240 each include a plurality of openings 132a-g, 232a-g, 142a-g, 242a-g, respectively, defined therethrough. Openings 132a-g, 232a-g of insulative plates 130, 230 and openings 142a-g, 242a-g of sealing plates 140, 240 are coaxially aligned with one another upon assembly thereof to respective metal support bases 120, 220. The electrically conductive sealing plates 140, 240 and the insulative plates 130, 230 include respective longitudinally-oriented knife slots 139, 239, 149, 249 defined therethrough for reciprocation of a knife blade (not explicitly shown). Openings 132a-g, 232a-g, 142a-g, 242a-g of insulative plates 130, 230 and respective sealing plates 140, 240 are disposed adjacent longitudinal knife slots 139, 239, 149, 249. Openings 132a-g, 232a-g, 142a-g, 242a-g are configured for receipt of respective ceramic stops 122a-g, 222a-g. Upon assembly of jaw members 110, 210, ceramic stops 122a-g, 222a-g protrude a distance from sealing plates 140, 240 to prevent sealing plates 140, 240 from touching and creating a short between sealing plates 140, 240. Upon assembly of jaw members 110, 210, ceramic stops 122a-g, 222a-g are adjacent blade slots 139, 239, 149, 249 to help grip tissue closer to where a division of the gripped tissue takes place, thus producing a more reliable cut.

In some embodiments, sealing plates 140, 240 may be affixed atop the insulative plates 130, 230, respectively, and metal support bases 120, 220, respectively, in any suitable manner, including snap-fit, over-molding, stamping, ultrasonic welding, etc. Metal support bases 120, 220, insulative plates 130, 230, and sealing plates 140, 240 are encapsulated by the outer insulative housings 102, 202 by way of an overmolding process. Insulative housings 102, 202 may be fabricated from various types of plastic materials, such as, for example, Amodel®, Trogamid®, PEKK, G-PEAK, PEEK, Thermotuff™, Ultem®, etc., all of which may be mineral and/or fiber reinforced.

During assembly, to form jaw member 110, metal support base 120 is formed and ceramic stops 122a-g are cut to a selected length. Insulative plate 130 is formed by injection molding and includes a longitudinal knife slot 139 formed therein. Sealing plate 140 is formed from a conductive material and has a longitudinal knife slot 149 formed therein. Openings 132a-g are formed in insulative plate 130 and openings 142a-g are formed in sealing plate 140 adjacent respective longitudinal knife slots 139, 149. Ceramic stops 122a-g are engaged to tissue-oriented surface 128 (i.e., directly connected to tissue-oriented surface 128) of metal support base 120 such that ceramic stops 122a-g extend substantially perpendicular from tissue-oriented surface 128. Insulative plate 130 is coupled to metal support base 120 by guiding and aligning insulative plate 130 along ceramic stops 122a-g until insulative plate 130 is in abutment with tissue-oriented surface 128 of metal support base 120. Sealing plate 140 is guided and aligned along ceramic stops 122a-g toward metal support base 120 until sealing plate 140 is in abutment with insulative plate 130 and second ends 127a-g of ceramic stops 122a-g protrude from sealing plate 140. Insulative housing 102 is overmolded around metal support base 120 to secure the components of jaw member 110 together. Jaw member 210 may be formed in a similar manner as jaw member 110, described above.

This process avoids using high temperatures traditionally used to connect ceramic stops 122a-g, 222a-g to a sealing plate 140, 240 of a jaw member 110, 210. Such high temperatures limit the materials that may be used for fabricating sealing plates 140, 240. Accordingly, the process of forming the jaw members 110, 210 disclosed herein allows for sealing plates 140, 240 to be constructed from alternative materials that would not be able to withstand high manufacturing temperatures normally utilized during the application of ceramic stops 122a-g, 222a-g to the sealing plates 140, 240. For example, the presently disclosed embodiments permit sealing plates 140, 240 to be constructed from a printed circuit board, which may provide additional benefits for surgical applications.

In one embodiment of the present disclosure, another process for assembling jaw members 110, 210 is provided. Instead of connecting ceramic stops 122a-g, 222a-g directly to metal support bases 120, 220 prior to coupling insulative plates 130, 230 and sealing plates 140 240 to metal support bases 120, 220, respectively, insulative plates 130, 230 and sealing plates 140, 240 are mounted to metal support bases 120, 220 prior to engaging ceramic stops 122a-g, 222a-g to metal support bases 120, 220. In particular, after insulative plates 130, 230 and sealing plates 140, 240 are mounted to metal support bases 120, 220, respectively, ceramic stops 122a-g, 222a-g are guided through respective openings 132a-g, 232a-g, 142a-g, 242a-g in insulative plates 130, 230 and sealing plates 140, 240 into engagement with the metal support bases 120, 220. In this way, ceramic stops 122a-g, 222a-g may be supported on metal support bases 120, 220 by being secured in openings 132a-g, 232a-g, 142a-g, 242a-g of insulative plates 130, 230 and sealing plates 140, 240. Ceramic stops 122a-g, 222a-g may be held in engagement with metal support bases 120, 220 via a friction-fit connection within openings 132a-g, 232a-g, 142a-g, 242a-g of insulative plates 130, 230 and/or sealing plates 140, 240. Similar to the method of assembling jaw members 110, 210 described above, this process avoids using high temperatures traditionally used to connect ceramic stops to a sealing plate of a jaw member.

Any of the components described herein may be fabricated from either metals, plastics, resins, composites or the like taking into consideration strength, durability, wearability, weight, resistance to corrosion, ease of manufacturing, cost of manufacturing, and the like.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to an operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

It will be understood that various modifications may be made to the embodiments of the presently disclosed jaw members and methods of forming said jaw members. Therefore, the above description should not be construed as limiting, but merely as exemplifications of embodiments. Those skilled in the art will envision other modifications within the scope and spirit of the present disclosure.

What is claimed is:

1. A method of forming a jaw member of an end effector, comprising;

providing a metal support base, an insulative plate having a plurality of openings defined therethrough, and a sealing plate having a plurality of openings defined therethrough;

directly connecting a first end of each of a plurality of ceramic stops to a tissue oriented surface of the metal support base, the ceramic stops having a predetermined length; and coupling the insulative plate and the sealing plate to the metal support base by aligning the plurality of ceramic stops through the plurality of openings defined in the insulative plate and the plurality of openings defined in the sealing plate such that a second end of each ceramic stop projects a predetermined distance relative to a tissue-engaging surface of the sealing plate.

2. The method according to claim 1, further comprising forming a longitudinal knife slot through each of the insulative plate and the sealing plate and aligning the slots in registration with one another.

3. The method according to claim 2, wherein the plurality of openings of the insulative plate and the plurality of openings of the sealing plate are formed adjacent each respective longitudinal knife slot.

4. The method according to claim 1, further comprising overmolding an insulative housing around the metal support base.

5. The method according to claim 1, wherein the insulative plate is formed by injection molding.

6. The method according to claim 1, wherein each of the plurality of ceramic stops has a cylindrical configuration.

7. The method according to claim 1, wherein each of the plurality of ceramic stops defines a longitudinal axis therealong and tissue-engaging surface of each of the plurality of ceramic stops defines a plane in perpendicular relation to each respective longitudinal axis.

8. The method according to claim 1, wherein the insulative plate is fabricated from plastic.

9. The method according to claim 1, wherein the predetermined distance is about 0.001 inches to about 0.006 inches.

10. The method according to claim 1, further comprising:
   moving the insulative plate and the sealing plate in a direction toward the plurality of ceramic stops; and
   moving the insulative plate and the sealing plate along the plurality of stops toward the metal support base.

* * * * *